United States Patent [19]
Schmitz

[11] Patent Number: 5,634,909
[45] Date of Patent: Jun. 3, 1997

[54] AUTO-RETRACTING NEEDLE INJECTOR SYSTEM

[76] Inventor: William L. Schmitz, 43901 Citrus View Dr., Hemet, Calif. 92544

[21] Appl. No.: 414,626

[22] Filed: Mar. 31, 1995

Related U.S. Application Data

[63] Continuation-in-part of Ser. No. 164,330, Dec. 9, 1993, abandoned.

[51] Int. Cl.$^6$ ..................................................... A61M 5/32
[52] U.S. Cl. ........................ 604/196; 604/110; 604/232; 604/201; 604/228
[58] Field of Search ........................... 604/110, 194–196, 604/201, 232, 228, 411, 414, 416

[56] References Cited

U.S. PATENT DOCUMENTS

| | | | |
|---|---|---|---|
| 2,895,474 | 7/1959 | Reznek | 604/228 |
| 3,115,135 | 12/1963 | Sarnoff | 604/228 |
| 3,897,491 | 7/1975 | Hurschman | 604/196 |
| 4,636,202 | 1/1987 | Lowin et al. | 604/236 |
| 4,808,169 | 2/1989 | Haber et al. | 604/195 |
| 4,931,040 | 6/1990 | Haber et al. | 604/110 |
| 5,098,382 | 3/1992 | Haber et al. | 604/110 |
| 5,167,641 | 12/1992 | Schmitz | 604/196 |
| 5,201,719 | 4/1993 | Collins et al. | 604/195 |
| 5,380,286 | 1/1995 | Van Den Haak | 604/110 |
| 5,415,648 | 5/1995 | Malay et al. | 604/181 |

*Primary Examiner*—Vincent Millin
*Assistant Examiner*—Bhisma Mehta
*Attorney, Agent, or Firm*—Ralph S. Branscomb

[57] ABSTRACT

A hypodermic injection system utilizes disposable medicament ampules having self-contained needles operated by a re-useable actuator to extend the needle from complete enclosure within the ampule out and into the flesh and inject the medicament as it moves, the needle automatically retracting into the disposable ampule after exhausting its contents, completely eliminating any need to handle the exposed needle before or after use. The post-injection needle retraction operation is powered by the reuseable actuator, avoiding the expense of prior devices which incorporate the retraction mechanism in the disposable ampule. The invention is useful to health professionals and also of particular utility to diabetics and others who must regularly self-inject.

10 Claims, 3 Drawing Sheets

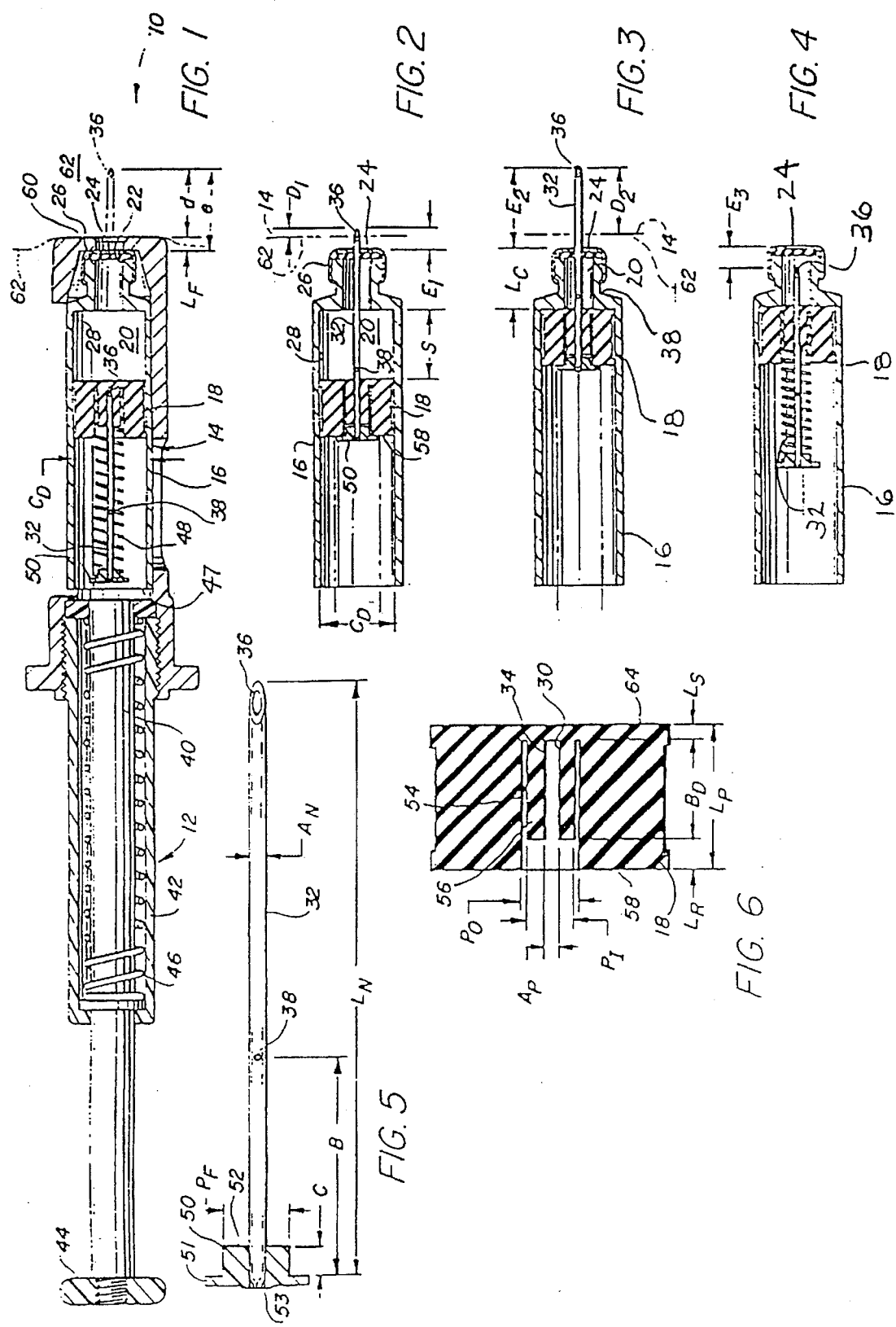

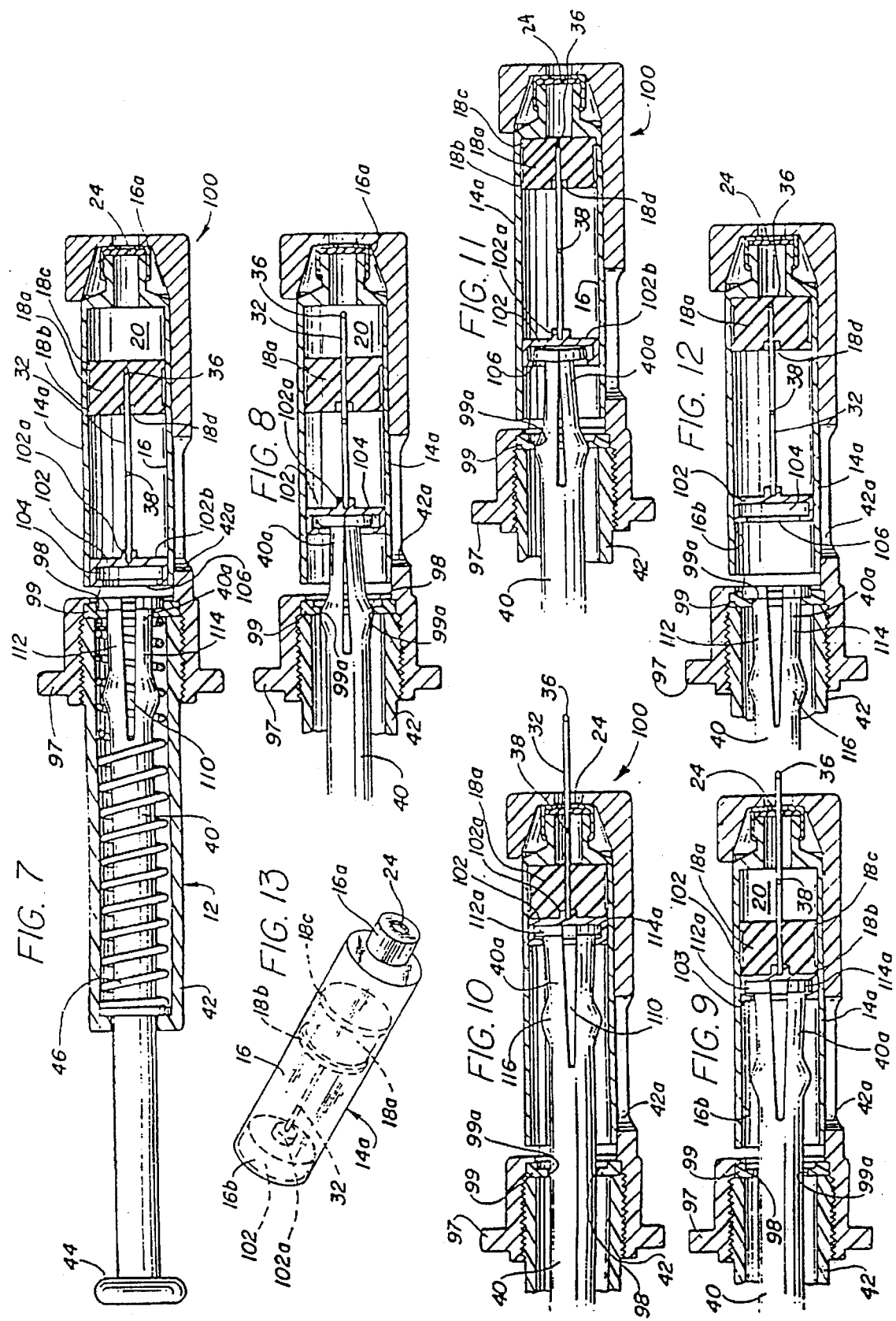

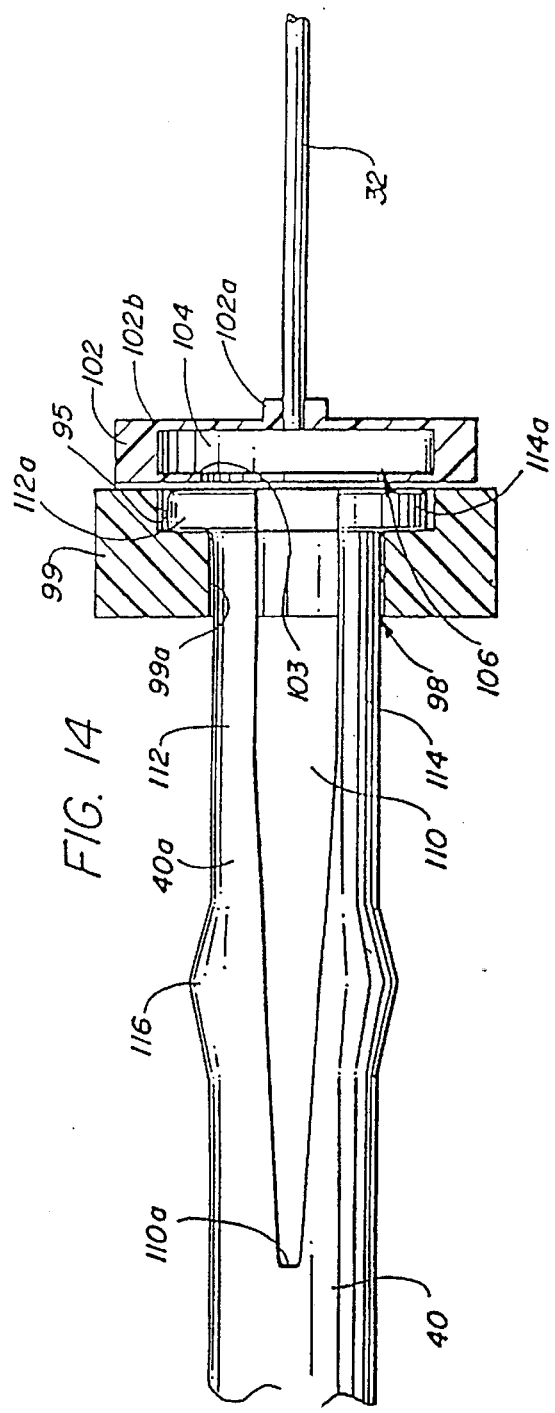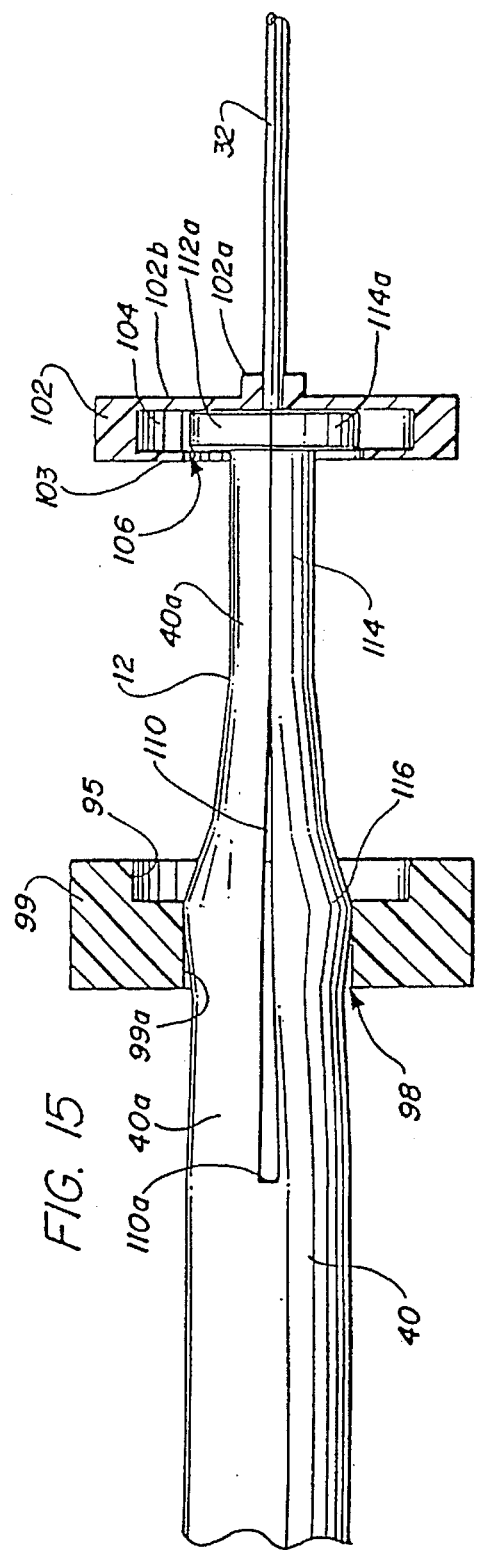

AUTO-RETRACTING NEEDLE INJECTOR SYSTEM

BACKGROUND OF THE INVENTION

This application is a CIP of application Ser. No. 08/164,330 filed Dec. 9, 1993 on an IMPROVED AUTO-RETRACTING NEEDLE INJECTOR SYSTEM by the same inventor, now abandoned, and also relates to the device issued on Dec. 1, 1992 under U.S. Pat. No. 5,167,641 by the instant inventor.

That disclosure pertained to a system similar to this one but incorporating the automatic post-use needle retract mechanism inside the disposable ampule rather than in the re-useable actuator. In addition to that disclosure, other injector devices for facilitating hypodermic injections are known, both for medicament ampules that are furnished with the injector device, and for conventional hypodermic syringes that are operated by the device. In the case of injection from self contained ampules, see, for example, U.S. Pat. Nos. 4,194,505, 4,316,463, and 4,413,991 to the present inventor, and U.S. Pat. No. 3,712,301 to Sarnoff. For injection from conventional syringes, see U.S. Pat. No. 4,494,358 to Fehlis; U.S. Pat. No. 3,7092,608 to Tibbs; and U.S. Pat. No. 3,880,163 to Ritterskamp, as well as the first above-identified patent.

It is also known to provide a "tracked" injection wherein the medicament is caused to issue from the needle as a continuous flow during movement of the needle into the patient's flesh for preventing tissue damage that would otherwise be caused by a "balloon" injection, wherein substantially all of the medicament is deposited after the needle reaches maximum penetration.

A problem with most syringe and ampule devices of the prior art is the danger of injury to the patient and others by the needle subsequent to the delivery of the medicament. (In the case of syringes, such danger is also present prior to medicament delivery.) Health care providers are accidentally but routinely scratched or punctured by the needle, being potentially harmed by residual quantities of the medicament, aside from the injury itself, and much more serious is the possibility that the needle may have become contaminated by body fluids containing HIV virus.

A number of syringes make provision for the retraction of the needle after use by linking the needle to the plunger and permitting retraction of the plunger by the physician's thumb, which withdraws the needle within the ampule, or disposable syringe body. These are passive systems that depend on the administering person to initiate, and to power, the withdrawal. If such person lays down the syringe without withdrawing the needle, the needle remains an extended invitation for an accident. There are so many needle accidents in the health care industry, all of which could have been prevented using safer procedures, that this is no trivial possibility, but in fact a reality. Without doubt, a syringe that depends on human action for needle withdrawal will be left exposed a certain percentage of the time, and a percentage of these oversights will result in puncture wounds.

It was for the purpose of overcoming this problem that the inventor developed the system that is disclosed in previously issued U.S. Pat. No. 5,167,641. The mechanism that this system uses is a retracting spring contained within the disposeable ampule which biases the needle into the retracted position in the ampule, and this is the place where the needle will allways be unless an outside force is being applied. When the force stops, the needle rretracts again. It is an approach which is highly effective in protecting patients and health professionals from exposed needles, but lacks the advantage of economic feasibility due to the expense of disposable ampules. Unlike the medicment, the retract mechanism could be re-used, and discarding the ampule with the spring mechanism in it escalates the cost of ampule production to demand-stifling levels. However, it did provide one solution to the human error problem, which the prior art did not.

But there is still a need for an injection system which has a hypodermic injector device that reliably and safely facilitates administration of a medicament dosage without subjecting the patient or others to contamination or injury from the device, without ignoring the reality of human error, one that is effective for delivery of medicament in a smooth tracked injection stroke begining at a predetermined depth just below the skin and continuing until exhausted, and that operates with disposeable ampules that are inexpensive enough to compete cost-wise with traditional ampules.

SUMMARY OF THE INVENTION

It is the objective of this invention to provide a safety injector system that meets the need discussed above, and as such it has several features, no single one of which is solely responsible for its desirable attributes. Without limiting the scope of this invention as expressed by the claims which follow, its more prominent features are as follows.

The invention includes an ampule having a housing that forms a portion of a medicament chamber and has a front opening in fluid communication with the chamber, a resilient closure member for sealingly closing the front opening, a resilient seal means for sealingly closing a rear portion of the chamber, and a tubular tissue-piercing needle movably supported within the housing for movement from a cocked position to an extended position, the needle having a front outlet and an inlet rearwardly located relative to and in fluid communication with the outlet; actuation means for advancing the needle from the cocked position to the extended position in response to external force and compressing the chamber for feeding the medicament from the chamber into the inlet and out of the outlet of the needle, and post-injection needle biasing means for biasing the needle rearwardly from the extended position, the ampule defining means permitting movement of the needle by the needle biasing means from the extended position to a final completely retracted position in response to removal of the external injectingforce. The outlet of the needle is completely enclosed within the chamber in the final withdrawn position for preventing accidental contact with the needle subsequent to use of the system, and withdraws to this position independantly of operator action, provided the operator soes not actively prevent the needle from withdrawing.

The central features of the system is that it uses a novel ampule that does not contain needle biasing means, and an actuator member interactive with the needle carried in the ampule but being separate from the ampule and carring the spring for autmatically retracting the needle indepemndently of both the ampule and the operator. The actuator member has a split plunger which extends forward with the two halves compressed together to insert into a socket defined in the rear of the ampule, where it expands to form a positive connection with the ampule as it advances the needle-carrying member from a cocked position where the needle is within the ampule to an extended position where the outlet tip of the needle pierces the seal means, closing the rear portion of the chamber to extend outward from the ampule.

Removing the external injecting force of the administrator automatically causes withdrawal of the needle into the ampule and then causes compression of the halves of the plunger, releasing the ampule from the actuator for removed and replacment. The elimination of the needle-retracting biasing means from within the ampule and incorporating compensating structure into the actuator simplifies the system and reduces the cost of the ampule to commercially feasible levels.

BRIEF DESCRIPTION OF THE DRAWINGS

The preferred embodiments of this invention, illustrating all its features, will now be discussed in detail. These embodiments depict the novel and non-obvious safety medicament injector system of this intention shown in the accompanying drawings which is for illustrative purposes only. These drawings includes the following figures, with like numerals indicating like parts:

FIG. 1 is a fragmentary sectional elevational view of a safety medicament injector system according to the present invention, the system including a medicament ampule, the ampule being shown in the cocked configuration;

FIG. 2 is a sectional elevational detail view showing the ampule of the system of FIG. 1 in an intermediate configuration;

FIG. 3 is a detail view as in FIG. 2, showing the ampule in an extended position;

FIG. 4 is a detail view as in FIG. 2, showing the ampule in a final retracted configuration;

FIG. 5 is a fragmentary longitudinal sectional view of a needle portion of the ampule of FIG. 1;

FIG. 6 is a longitudinal sectional view of a piston of the ampule of FIG. 1;

FIG. 7 is a fragmentary sectional elevational view of an alternate embodiment of the safety medicament injector system according to the present invention, the system including a medicament ampule with an internal needle carrying member in a cocked position;

FIG. 8 is a fragmentary sectional elevational view of the alternate embodiment shown in FIG. 7, showing an actuator member interacting with the needle carrying member in response to an external force to move the needle carrying member from the cocked position;

FIG. 9 is a fragmentary sectional elevational view of the alternate embodiment shown in FIG. 7, showing the actuator member as it pushed the outlet of the needle through a seal closing the rear portion of the ampule's medicament chamber;

FIG. 10 is a fragmentary sectional elevational view of the alternate embodiment shown in FIG. 7, where the actuator member has pushed a sealing piston and the needle carrying member to the forward end of the ampule, forcing essentially all the medicament from the ampule's medicament chamber;

FIG. 11 is a fragmentary sectional elevational view of the alternate embodiment shown in FIG. 7, where the actuator member is withdrawn, carrying with it the needle carrying member and withdrawing the outlet tip of the needle into the sealing piston;

FIG. 12 is a fragmentary sectional elevational view of the alternate embodiment shown in FIG. 7, showing the actuator member withdrawn from the ampule;

FIG. 13 is a perspective view of the novel ampule used in the alternate embodiment of this invention shown in FIG. 7;

FIG. 14 is a simplified, enlarged view of the end of the plunger in the cocked position;

FIG. 15 is a simplified, enlarged view of the end of the plunger in the active position.

DETAILED DESCRIPTION OF THE PREFERRED EMBODIMENTS

The present invention is directed to a hypodermic injector system for safely administering a medicament to a patient without hazardous exposure of the patient or medical providers to contamination or injury following use of the system. For purposes of providing a smoothe transition from the prior invention of the inventor, the first portion of this application parallels that of the above-referenced U.S. Pat. No. 5,167,641 pertaining to the device with the retractor in the ampule, with the preferred and claimed embodiment being shown in FIGS. 7–15.

In FIGS. 1–6, the injector system 10 includes an actuator 12 and a disposable ampule 14 removably received therein. The ampule 14 has a housing or body 16 and a piston 18 sealingly axially movable therein for defining a variable volume chamber 20. A front opening 22 of the body 16 is sealingly closed by a resilient disk-shaped closure member 24, the closure member 24 being retained on the body 16 by a crimped band 26 in a conventional manner.

The piston 18 is formed of a suitable elastomer for sealing contact with a bore 28 of the body 16, and having a passage 30 formed therein for guiding a tubular needle 32 that is carried by the piston 18, the passage 30 being separated from the chamber 20 by a seal portion 34 of the piston 18, the needle 32 being sharpened at a forward end outlet 36 thereof for piercing the seal portion 34 and the closure member 24 as described below, the outlet 36 being located proximate the seal portion 34 in a cocked position of the needle 32 as shown in FIG. 1. The needle 32 has a side inlet 38 formed therein, the inlet 38 being in fluid communication with the outlet 36 for delivery of the medicament from the chamber 20 when the inlet 38 is within the chamber 20 as shown in FIGS. 2 and 3.

The needle 32 is advanced from the cocked position of FIG. 1 to an extended position (shown in FIG. 3) by a plunger 40 of the actuator 12, the plunger 40 being axially slidably supported in a frame 42 of the actuator 12 and having a handle 44 fixably connected at a rear extremity thereof for receiving an external actuating force from an operator of the system 10. The plunger 40 is biasingly connected to the frame 42 by a helical compression plunger spring 46 for moving rearwardly from the needle 32 upon removal of the external force.

An important feature is that the needle 32 is biased rearwardly for retraction into the body 16 when the plunger moves rearwardly from the needle 32. For this purpose, a helical compression needle spring 48 is interposed between the piston 18 and a flange member 50 that is rigidly connected to the rear extremity of the needle 32, the flange member 50 having an outer flange portion 51, and a body portion 52 that extends into a rear extremity of the needle spring 48 for locating same. The piston 18 has a cylindrical spring cavity 54 formed therein for receiving a front portion of the needle spring 48, the passage 30 being formed within a boss portion 56 of the piston 18, the boss portion 56 being concentrically spaced within the spring cavity 54 and terminating forwardly of a rear face 58 as shown in FIGS. 2 and 3. The rear extremity of the needle 32 is sealingly crimped closed as indicated at 53 in FIG. 5, the crimped portion 53 also serving to anchor the flange member 50 on the needle 32.

As shown in FIG. 1, the ampule 14 is retained axially behind a flange portion 60 of the frame 42 of the actuator 12, the flange portion 60 having an axial flange length $L_F$. The needle 32 projects by a variable extension distance e forwardly of the ampule 14 in response to operation of the plunger 40, and by a corresponding penetration depth d from the flange portion 60 into an injection site 62 of the patient. As further shown in FIG. 2, the needle extends forwardly of the ampule 14 by a first or initial extension distance $E_1$ (and into the injection site 62 by a corresponding initial depth $D_1$) when the flange member 50 initially contacts the rear face 58 of the piston 18, the piston 18 being movable forwardly from its initial position by a stroke S in sliding engagement with the bore 28 of the body 16, the bore 28 having a chamber diameter $C_D$. As shown in FIG. 3, when the piston 18 is moved fully forward within the bore 28, being located behind the front of the ampule 14 by an axial front cylinder length $L_C$, the needle 32 extends forwardly of the ampule 14 by a second distance $E_2$. (and into the injection site 62 by a second corresponding full depth $D_2$. Following removal of the external force as described above, the needle 32 is retracted by the needle spring 48 to a distance $E_3$ within the ampule 14 as shown in FIG. 4.

As shown in FIG. 6, the piston 18 has an overall piston length $L_P$ between a front face 64 and the rear face 58, the seal portion 34 being flush with the front face 64 and having a wall thickness or seal length $L_S$, the spring cavity 54 also extending to the same distance from the front face 64. The spring cavity 54 is formed with a cavity outside diameter $P_o$ and a cavity inside diameter $P_I$ for clearing the needle spring 48, the passage 30 within the boss portion 56 having a passage diameter AP, the boss portion 56 extending to a boss depth $B_D$ from the rear face 58 of the piston 18. As shown in FIG. 5, the needle 51 forwardly to the end outlet 36, the body portion 52 extending forwardly of the flange portion 51 by a body distance C and having a flange body diameter $P_F$. The side inlet 38 of the needle 32 is located forwardly of the flange portion 51 by an inlet distance B.

The inlet distance B is slightly greater than the piston length $L_P$ for excluding the medicament from the needle 32 until the flange member 52 is nearly seated against the rear face 58 of the piston 18. Also, the distance $L_R$ is slightly greater than the body distance C for permitting the flange portion 51 to seat against the rear face 51. Thus, the initial extension distance $E_1$ in FIG. 2 is equal to the needle length $L_N$ less the total of the piston length LP, the flange length $L_C$, and the stroke S. Correspondingly, the initial penetration depth $D_1$ is the first extension distance $E_1$ reduced by the flange length $L_F$ of the flange portion 60. Similarly, the full extension distance $E_2$ of FIG. 3 is equal to the length $L_N$ reduced by the piston length $L_P$ and the distance $L_C$, the corresponding full penetration depth $D_2$ being the full extension distance $E_2$ rescued by the flange length $L_F$.

Preferably, the initial penetration depth $D_1$ is approximately 0.09 inch for avoiding loss of the medicament from the injection site 62. Also, a conveniently configured combination of the body 16, the closure member 24, and the band 26 has the distance $L_C$ being approximately 0.3 inch. For operation with the chamber diameter $C_D$ in the range of between approximately 0.25 inch to approximately 0.385 inch, which is sufficient for accommodating the needle spring 48 in its compressed condition as described below. A preferred configuration of the needle 32 and the flange member 50 has the needle length $L_N$ being approximately 1.2 inches, the inlet distance B being approximately 0.45 inch for use with the body 16 and the piston 18 configured as described above.

The tracked injection feature of the present invention is obtained by entry of the side inlet 38 of the needle 32 into the chamber 20, ahead of the piston 18 as shown in FIG. 2, before the needle 32 reaches the extended position of FIG. 3, whereby the medicament flows from the chamber, through the needle 32, and into the flesh at the injection site 62 during forward movement of the piston 18. In a preferred first, exemplary embodiment of the present invention providing a volummetric medicament capacity of ½ cc of the ampule 14, the chamber diameter $C_D$ is about 0.4 inch in diameter, the stroke S of the piston 18 being about 0.39 inch.

The present provides a safe and convenient solution to the problem of administering injections by those not having specialized medical training. The system 10 can easily be operated by the person receiving the injection, and the targeted injection site 62 does not need to be in view. Moreover, the injection is quick and painless. Most importantly, the needle 32 retracts automatically into the ampule 14 upon release of the plunger 40, thereby avoiding the special hazards associated with accidental exposure to the needle 32 subsequent to operation of the system 10.

The springs 46 and 48 are fabricated from a suitable spring-tempered material such as corrosion-resistant steel. In a preferred configuration of the ampule 14, the needle spring 48 is formed of 0.020 inch diameter steel as described above, having 15 turns at approximately 12.6 turns per inch on an approximately 0.230 inch pitch diameter. The needle spring 48 has a free length of approximately 1.19 inch, and a solid length approximately 0.30 inch, opposite ends of the spring 48 within the piston 18 is obtained with the cavity outside diameter $P_o$ of the spring cavity 54 being approximately 0.256 inch, the cavity inside diameter $P_I$ being approximately 0.204 inch. The piston 18 and the closure member 24 can be made from conventional silicon rubber formulations. The other parts of the system 10 are preferably molded from a suitable plastic material for light weight and ease of fabrication. Suitable plastic materials for the system 10 include ABS, polycarbonate, and acetyl.

This Improvement invention, the system 100, is illustrated in FIGS. 7-12. The major differences between the this and the prior invention are (i) the elimination of the helical compression needle spring 48, (ii) the replacement of the flange member 50 by a socket member 102, (iii) the utilization of a simplified piston 18a, and (iv) the modification of the plunger 40 so that it is coupled to the socket member to push the needle out from the ampule for injection and then withdrawal back into the ampule, and then de-coupled after the needle is safely withdrawn into the ampule. Like the prior embodiment, the system 100 includes the frame 42 having a actuator 12 holding the plunger 40 which has the plunger spring 46 biasing the plunger 40 outward from the frame, and an ampule 14a removably received within the frame 42 adjacent an open window 42a in the frame 42.

The second embodiment has a collar 99 attached to the frame 42 by a threaded coupling 97. As best shown n FIGS. 14 and 15, the collar 99 has an internal circular rim 99a defining an opening 98 in the collar and a bore 95 in the proximal face of the collar. The rim 99a serves as a cam actuator as will be discussed in detail subsequently. The plunger 40 is shown in a cocked position in FIG. 14, with the spring 46 urging the plunger outward to the position shown in FIG. 7. The one end 40a of the plunger 40 is designed to move through the opening 98 when the operator pushes against the handle 44 to advance the plunger towards the ampule 14a. FIG. 15 shows the plunger 40 in an active position where the end 40a has been moved to a forward position engaging the socket member 102 by the operator applying an external force.

In accordance with this invention, the ampule 14a includes the body 16 which may be made of a translucent or transparent material such as glass or plastic. One end 16a of the body 16 is sealed essentially identically to the ampule 14 depicted in FIG. 1. The other end 16b of the ampule 14a is open so that the end 40a of the plunger 40 may enter this end when the operator advances the plunger. The socket member 102 is seated within the body 16 with its perimeter pressing snugly against the inner surface of the body 16, but free to move reciprocally and axially within the body 16. Thus, the internal wall of the body 16 acts as a guide for the socket member 102 as this member moves toward the end 16a. The needle 32 is securely fastened, for example by crimping and bonding with an adhesive as illustrated in the first embodiment, to a raised nipple portion 102a of the socket member 102. The needle 32 extends outward at a right angle to the inner face 102b of socket member. This socket member 102 is a molded plastic component having an internal, cylindrical cavity 104 with an open, circular entryway 106 in the outer face of the socket member. The entryway 106 is concentric with the cavity 104, and the longitudinal axis of the needle 32 intersects the center of the entryway and cavity. An annular wall 103 restricts the entryway 106, so that the diameter of the entryway is slightly less then the internal diameter of the cavity 104. As shall be discussed in greater detail subsequently, the end 40a of the plunger is adapted to enter the cavity 104 when the plunger is advanced.

The piston 18a is similar to piston 18, but greatly simplified because the needle spring 48 is eliminated. The piston 18a is configured like a spool, having a reduced diameter central section having at its opposed ends raised edges 18b and 18c providing a seal between the inner wall of the body 16 and the perimeter of the piston 18a, so that medicament is contained in the chamber 20. The outer face of the piston 18a has a central recess 18d into which the forward end of the needle extends, partially penetrating the piston in the cocked position, as depicted in FIG. 7. In the cocked position, the outlet 36 of the needle 32 is covered by the body of the piston 18a, but does not pierce it and enter the chamber 20. the inlet 38 is uncovered since the needle has not been completely pushed through the piston 18a. Crimping closed the rear end of the needle 32 so that medicament only enters the needle through the inlet 38. The distance between the inlet 38 and the outlet 36 is precise to insure that the inlet 36 enters the chamber 20 simultaneously with the outlet penetrating the closure member 24 when the operator advances the plunger 40 into the body 16 of the ampule 14a.

The plunger end 40a is adapted to grip the socket member 102 upon advancing the plunger 40 into the open ampule end and release this grip when the external force is removed. As illustrated in FIGS. 14 and 15, the plunger end 40a is split lengthwise to form a normally open, V-shaped mouth 110 surrounded by a pair of jaws 112 and 114. There are raised lips 112a and 114a, respectively at the ends of each jaw 112 and 114, and a raised cam section 116 in the circumference of the plunger 40 near the lips 112a and 114a, between the bite 110a of the V-shaped mouth 110 and the lips. The lips 112a and 114a have a thickness slightly less than the depth of the cavity, and these lips are seated in the bore 95 when the plunger 40 is in the cocked position as shown in FIG. 14.

As illustrated in FIGS. 8, 11, and 15, when the cam section 116 engages the rim 99a, the normally open mouth 110 is closed, bringing the jaws 112 and 114 together. Closure of the jaws 112 and 114 brings the lips 112a and 114a together as depicted in FIGS. 8, 11, and 14 to allow these lips to clear the open entryway 106 of the cavity 104.

In FIGS. 8 and 15, the closed lips 112a and 114a are shown immediately after entering the cavity 104. In FIG. 11, the closed lips 112a and 114a ar shown just prior to exiting the cavity 104. The material forming the plunger 40 creates an internal spring force which causes the jaws 112 and 114 to return to the normally open position shown in FIG. 7 once the cam section 116 clears the rim 99a. The plunger 40 is made of a plastic which is both rigid and sufficiently resilient to permit the jaws 112 and 114 to open when not being closed by the cam section 116 engaging the rim 99a. With the jaws 112a and 114a open and lodged in the cavity 104 as shown in FIG. 9, the plunger 40 and socket 102 are coupled together and move as a unit.

The system 100 is easy to use. The operator places the ampule 14a with medicament filling the chamber 20 into the frame 42 in axial alignment with the plunger 40. Next, the operator grasps the frame 42, with the index and middle finger straddling the frame and the thumb overlying the handle 44, and positions the seal 24 against the flesh of the patient. The operator then applies an external force to the handle 44, pushing the plunger 40 towards the open end 16b of the ampule 14a to overcome the biasing force of the spring 46, moving the socket member 102 from the cocked position shown in FIG. 7.

As depicted in FIGS. 8 and 15, as the plunger 40 is advanced, the cam section 116 engages the rim 99a of the collar 99 to close the jaws 112 and 114 to enable the lips 112a and 114a to pass through the entryway 106 and enter the cavity 104 in the socket member 102. Upon further advancement of the plunger 40, the cam section 116 clears the rim 99a and the jaws 112a and 114a open after entry into the cavity 104, so that the plunger 40 results in moving the socket member 102 towards the piston 18a, pushing the needle 32 deeper into the piston 18a until the outlet 36 moves into the chamber 20 as shown in FIG. 8.

The operator continues to advance the plunger 40, which moves the socket member 102 axially deeper into the body 16 of the ampule 14a until the socket member engages the piston 18a. Upon engagement, the nipple 102a is seated in the recess 18d as shown in FIG. 9. After this engagement and with continual advancement, the plunger 40 pushes against the piston 18a to move the piston towards the closure member 24, compressing the liquid medicament within the chamber 20. The system 100 is now ready to inject the medicament into the flesh of the patient. The system 100 is designed to provide track injection of the medicament, immediately introducing a portion of the medicament in the chamber 20 into the flesh of the patient as the outlet 36 of the needle 32 pierces the patient's flesh.

As depicted in FIG. 9, the distance between the outlet 36 and inlet 38 is predetermined so that the outlet 36 pierces the closure member 24 at precisely the same time that the inlet 38 enters the chamber 20. Prior to the needle puncturing the closure member 24, the pressure within the chamber 20 is equal to ambient air pressure and the medicament cannot flow in a reverse direction into the outlet 36. With the needle 32 in the position shown in FIG. 9, medicament flows under pressure into the inlet 38 and out the outlet 36 into the flesh of the patient. The operator continues to advance the plunger 40, forcing essentially all the medicament out the outlet 36 until the piston 18a reaches the position shown in FIG. 10.

At this point when the medicament has been discharged from the chamber 20, the operator releases the thumb pressure being applied to the handle 44. The spring 46 immediately returns the plunger 40 to the cocked position shown in FIG. 7, pulling the socket member 102 with attached needle 32 into the body 16 of the ampule 14a as shown in FIG. 11. The piston 18a remains stationary adjacent the closure member 24. The force of the spring 46 is sufficient to overcome the internal spring force of the plunger material. Consequently, the cam section 116 is pulled by the spring 46 past the rim 99a to cause the lips 112a and 114a to be pressed together as depicted in FIGS. 11 and 15 and pulled through the entryway 106 and returned to the position shown in FIG. 12, where the jaws 112 and 114 are opened by the internal spring force of the plunger material. The plunger 40 has now cleared the open end 16b of the ampule 14a and releases its grip on the socket member 102, allowing the operator to remove the empty ampule from the frame 22 by simply inserting a finger through the open window 42a and pushing against the ampule. Another ampule 14a filled with medicament can now be inserted into the frame 42.

In accordance with an important feature of this invention, the distance between the cam section 116 and the lips 112a and 114a is carefully adjusted, so that when the plunger 40 releases its grip on the socket member 102, the outlet 36 is left lodged within the body of the piston 18a as shown in FIG. 12. This contaminated outlet tip 36 is thus safely embedded within the piston 18a so that it cannot accidentally stick anyone.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. For example, the ampule 14 can be made in other sizes for providing different medicament volumes. Also, the flange member 50 can be enlarged such that it is guided by the bore 28, and the boss portion 56 of the piston 18 can be formed as a rearward extension from the rear face 58 of the piston 18, particularly when the chamber diameter $C_D$ is very small. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

It is hereby claimed:

1. A medicament injector for use injecting medicament from a disposeable ampule into a patient, withdrawing the ampule needle into the ampule, and ejecting the ampule, said injector being intended for use with an appropriate ampule which has the following characteristics:
   (i) an end and a seal closing said end, and
   (ii) being filled with medicament and disposable after discharge of the medicament, and
   (iii) including a needle-carrying member which carries a needle having:
      (j) a sharp outlet tip adapted to pierce said seal, and
      (jj) an inlet spaced from said outlet tip such that said medicament can flow into said inlet in the needle and out the tip after said tip pierces said seal;
   said injector comprising:
   (a) a housing configured to,
      (i) releasibly receive said appropriate ampule, and
      (ii) discharge same after use, and
   (b) an actuator connected to the housing and having coupling means which is interactive with the needle carrying member of said ampule in response to an external force to advance the needle carrying member from a cocked position in which the needle is within the ampule to an extended position in which the tip of the needle pierces the seal and extends outward from the ampule;
   (c) spring means biasing said actuator toward said cocked position in said housing;
   (d) said coupling means positively coupling with said needle carrying member of said ampule when said needle is in said extended position, and upon removal of the external force, withdrawing the needle carrying member and needle back into the ampule under action of said spring means so that the tip of the needle is within the ampule; and,
   (e) said coupling means including means for decoupling from the needle carrying member when the tip of the needle has been withdrawn into the ampule.

2. The injector of claim 1 where the coupling means comprises:
   (a) a plunger movable from a cocked position to an extended position with said spring means biasing the plunger to return to the cocked position, said plunger having:
      (i) a gripping section movable by lateral displacement between gripping and ungripping positions; and,
      (ii) a cam section rearward of the gripping section; and
   (b) a cam actuator which engages the cam section as the plunger moves between the cocked and extended positions to deflect said gripping section;
   (c) said needle carrying member defining laterally extended structure and said plunger being advanced by the external force which overcomes the bias of said spring means to move the cam section past the cam actuator, thereby laterally deflecting the gripping section to move into the gripping position to grasp the laterally extended structure of said needle carrying member and advance the needle carrying member from the cocked position to the extended position; and,
   (d) upon removal of the external force, said spring means returning the plunger to its cocked position, pulling the cam section past the cam actuator to move the gripping section to its ungripping position to release the needle carrying member after the tip of the needle has been withdrawn into the ampule.

3. For use with said approrpriate ampule of claim 1 wherein said seal is a piston seal, an injector according to claim 2 wherein the distance between the cam section and the gripping section is selected to cooperate with the dimensions of the ampule as seated in the housing of said injector so that the tip of the needle is lodged within said piston seal in the ampule when said injector is in the cocked position.

4. An injector system comprising:
   (a) an ampule having:
   (b) an elongated hollow body having a front extremity;
   (c) a pierceable seal closing said front extremity;
   (d) a piston sealingly slidably disposed in said body to the rear of said seal;
   (e) a medicament chamber formed in said body between said piston and said seal; and,
   (f) a tubular syringe needle axially slidably supported in said piston and having a forward tissue-piercing tip defining a medicament outlet and an inlet rearwardly spaced from said outlet;

(g) a needle-carrying member carrying said needle; and, (h) an actuator having, (I) a housing to releasibly receive said ampule;

(j) a plunger axially slidable in said housing in substantial axial alignment with said ampule and movable from a rearward cocked mode to advance said needle and said plunger in said housing until said needle tip pierces said seal and penetrates the skin of a patient;

(k) coupling means for positively engaging said needle-carrying means by said plunger; and, (l) spring means biasing said plunger rearwardly within said housing to withdraw said needle into said ampule body after an injection has been made.

5. An injector system according to claim 4 wherein said coupling means includes decoupling means to release said needle carrying member as same withdraws to said cocked mode.

6. An injector system according to claim 5 wherein said coupling means comprises:

a plunger having a forward end defining at least one laterally deflectable tine having a forward tip with a lateral lip, and a corresponding lateral extension axially aligned with said lip defined by said needle carrying member such that said tine can be laterally deflected to hook said lip around said extension, and cooperating cam means defined on said plunger and said actuator such that upon forward movement of said plunger toward said ampule said tine is deflected and hooks said extension for positive engagement thereof, and withdrawal of said plunger again deflects said tine to release said tine.

7. An injector system according to claim 6 wherein said at least one tine are plural and in a closely spaced radial array radially inwardly compressible and said needle carrying member defines a rearwardly directed socket with an entryway thereto and an inwardly directed rim at said entryway which defines said lateral extension to engage the lips of said at least one tine as same enter said socket while compressed together, and then expand.

8. An injector system according to claim 7 wherein said cooperating cam means comprises a ring cam actuating surface defined by said housing through which said plunger passes and ramped cams defined by radial outer surfaces of said tines.

9. An injector system according to claim 7 wherein said housing defines a laterally accessible ampule compartment into which ampules are inserted for use and from which same are ejected for disposal, and the axial spacing of the cam means, housing and ampule is such that when said plunger is in said cocked mode it is clear of said ampule to free it for lateral removal.

10. A medical injector system comprising:

(a) an ampule including:

(I) a hollow cylindrical body having an open rear end and a sealed forward end which may be pierced by a needle;

(ii) a piston within said body between said ends which defines and seals a medicament chamber;

(iii) said piston being movable from a cocked position to a forward position in close proximity to said sealed end;

(iv) a needle having a side inlet and a connector member attached to the rear end of said needle, and said needle having a forward outlet end embedded in the piston; and, (v) said needle being moveable axially within the chamber as the piston moves between the cocked position and the forward position; and, (b) an actuator which removably receives the ampule and defines a rearwardly biased plunger and a spring rearwardly biasing same, said plunger having releasible positive engagement means to couple with said connector member when said plunger moves forwardly under application of an external forwardly-directed force on said plunger, into the open end of the ampule and positively engages the connector member for first advancing the outlet end through the piston and then through the seal at the same time that the inlet moves into communication with the chamber to force medicament from the chamber out the outlet end as a tracked injection when the needle reaches an extended position, piercing the seal and entering the patient, and, (c) said plunger, being biased by said spring to move rearwardly, away from said sealed end into the normally retracted, cocked position, and, upon release of the external force, releasing the positive engagement between said plunger and the connector after the needle has been retracted into the ampule, with the forward end lodged in the piston.

\* \* \* \* \*